(12) United States Patent
Dwyer et al.

(10) Patent No.: US 8,940,033 B2
(45) Date of Patent: Jan. 27, 2015

(54) METHOD AND APPARATUS FOR WHITENING TEETH

(75) Inventors: Joe Dwyer, Holly, MI (US); Kaya Bromley, Lapeer, MI (US)

(73) Assignee: Whiten, LLC, Imlay City, MI (US)

( * ) Notice: Subject to any disclaimer, the term of this patent is extended or adjusted under 35 U.S.C. 154(b) by 106 days.

(21) Appl. No.: 13/369,835

(22) Filed: Feb. 9, 2012

(65) Prior Publication Data

US 2012/0214122 A1    Aug. 23, 2012

Related U.S. Application Data

(60) Provisional application No. 61/444,304, filed on Feb. 18, 2011.

(51) Int. Cl.
| | | |
|---|---|---|
| *A61C 5/14* | (2006.01) | |
| *A61N 5/06* | (2006.01) | |
| *A61C 19/06* | (2006.01) | |

(52) U.S. Cl.
CPC .................. *A61C 19/066* (2013.01)
USPC ............. 607/88; 433/29; 433/37; 362/249.02

(58) Field of Classification Search
CPC ............ A61C 1/00; A61C 9/00; F21S 21/00; F21V 21/00
USPC .................. 433/29, 37; 362/249.02
See application file for complete search history.

(56) References Cited

U.S. PATENT DOCUMENTS

| | | | |
|---|---|---|---|
| 4,661,070 A | 4/1987 | Friedman | |
| 5,316,473 A | 5/1994 | Hare | |
| 6,391,283 B1 | 5/2002 | Jensen et al. | |
| 6,616,447 B1 * | 9/2003 | Rizoiu et al. | 433/29 |
| 6,733,290 B2 | 5/2004 | West et al. | |
| 6,976,841 B1 * | 12/2005 | Osterwalder | 433/29 |
| 7,160,111 B2 | 1/2007 | Baughman | |
| 7,331,784 B2 * | 2/2008 | Suzuki | 433/29 |
| 7,621,746 B2 | 11/2009 | Baughman | |
| 7,645,137 B2 | 1/2010 | Wasyluch | |
| 8,029,278 B1 | 10/2011 | Levine | |
| 8,172,570 B2 * | 5/2012 | Baughman | 433/29 |
| 2008/0057464 A1 * | 3/2008 | Rose et al. | 433/29 |

FOREIGN PATENT DOCUMENTS

WO    WO 2007006875 A1 *  1/2007

* cited by examiner

*Primary Examiner* — William Thomson
*Assistant Examiner* — Victor Shapiro
(74) *Attorney, Agent, or Firm* — Gifford, Krass, Spinkle, Anderson & Citkowski, P.C.

(57) ABSTRACT

An apparatus for whitening teeth comprises a mouth tray comprising a horseshoe-shaped trough sized to accommodate a dental ridge. A planar projection extends from the outer side of the trough so that its far end is external of the mouth. A light box containing a plurality of LEDs couples with the external end of the projection and illuminates the projection end. The mouth tray and projection are formed of a light-transmissive material to irradiate a peroxide gel in the trough to whiten the user's teeth.

13 Claims, 4 Drawing Sheets

US 8,940,033 B2

METHOD AND APPARATUS FOR WHITENING TEETH

CROSS-REFERENCE TO RELATED APPLICATIONS

This application claims priority of U.S. Provisional Patent Application 61/444,304 filed Feb. 18, 2011, the contents of which are incorporated herein by reference.

FIELD OF THE INVENTION

This invention relates to methods and apparatus for whitening surfaces of teeth employing an intra-oral mouth tray having a trough shaped to accommodate a toothed ridge, formed of light-conductive materials which may be filled with whitening gels and an extra-oral light source based on laser diodes which mates with the trough to apply the radiation from the LEDs to the material in the trough.

BACKGROUND OF THE INVENTION

The aesthetic value of whitened visible tooth surfaces has led to the development of a number of techniques for whitening ranging from the application of plastic veneers to the visible surfaces of the teeth to whitening toothpastes.

Many of these techniques employ bleaching involving the application of gels to the visible teeth surfaces. The gels break down either over time or at an accelerated rate by the application of radiant energy to produce byproducts operative to oxidize the discolored tooth surfaces and produce whitening. The bleaching compounds typically employ forms of peroxide and are often applied using trough-like mouth trays which may be filled with the gel-like peroxide compounds so that all of the visible surfaces of a patient's teeth are whitened at the same time.

Radiation may be directed at the gel covered teeth surfaces to accelerate the decomposition of the gels. A variety of systems have been proposed for applying radiant energy to the gels within an oral tray such as the systems shown in U.S. Pat. No. 7,645,137 and U.S. Pat. No. 8,029,278. These systems generally provide intra-oral light sources, either within or on the outer side of the trays containing the gels. The power sources for these lights may be either battery power or power applied from a source outside the mouth which is connected into the mouth.

The application of electric power for the illumination sources within the mouth is problematic. The user of the device is required to bite the tray and there exists a danger of applying the electrical potentials used to power the lights into the patient's mouth. The illumination sources are also fragile and the oral pressures applied during the use of the device may break them. Moreover, while the devices are often used in dentists' offices, it would be desirable to provide a system simple and safe enough to be adaptable for home use so that it could be employed by consumers to periodically perform the whitening process and thereby maintain a highly aesthetic look over extended periods of time.

SUMMARY OF THE INVENTION

The present invention is broadly directed to such a system. A preferred embodiment of the system of the present invention, which will subsequently be described in detail, broadly consists of a horseshoe shaped, trough-like mouth tray formed of a material that is transparent or translucent to radiation of a wavelength capable of accelerating the whitening process. The trough is adapted to be filled with any conventional tooth whitening gel, preferably of the peroxide type. The tray has a base section which extends forwardly of the trough, so that the trough may be filled with gel, inserted into a user's mouth so that the user's teeth are disposed within the trough with the user's lips closed about the top and the bottom of the forwardly extending base section. The forward end of the base section terminates in a male dovetail shape.

The entire tray, trough, base, and dovetail are preferably formed of a relatively soft medical grade silicone or plastic material that is transparent to and internally transmissive of light of an appropriate wavelength. In the case of the preferred embodiment, this light is produced by blue LEDs having a 450-500 nm dominant wavelength.

The male dovetail, which extends upwardly at the forward end of the trough base, is adapted to be inserted within a complementary female dovetail formed at one end of a generally rectangular light source. The light source preferably contains a series of blue LEDs arranged at regular intervals adapted to illuminate the forward edge of the male dovetail. The LEDs are powered by a 1.5 volt rechargeable battery which feeds a voltage multiplier current supported on a printed circuit board within the light source. A switch on the light source controls the powering of the LEDs and when illuminated the LEDs transmit light through the male dovetail section of the trough extension into the base and upwardly through the trough walls so that all sides of the teeth are irradiated by the light.

BRIEF DESCRIPTION OF THE DRAWINGS

Other objects, advantages, and applications of the present invention will be made apparent by the following detailed description of a preferred embodiment of the invention. The description makes reference to the accompanying drawings in which.

DETAILED DESCRIPTION OF THE PREFERRED EMBODIMENTS

Figure 2:
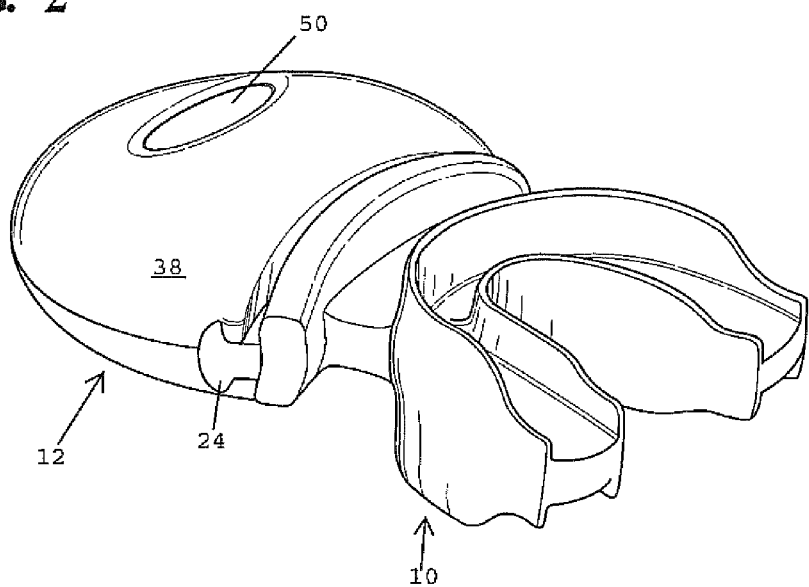
FIG. 2 is a perspective view from the rear top of a preferred embodiment of the invention with the two sections, the trough-like mouthpiece and the light box, engaged with one another.
Figure 3:
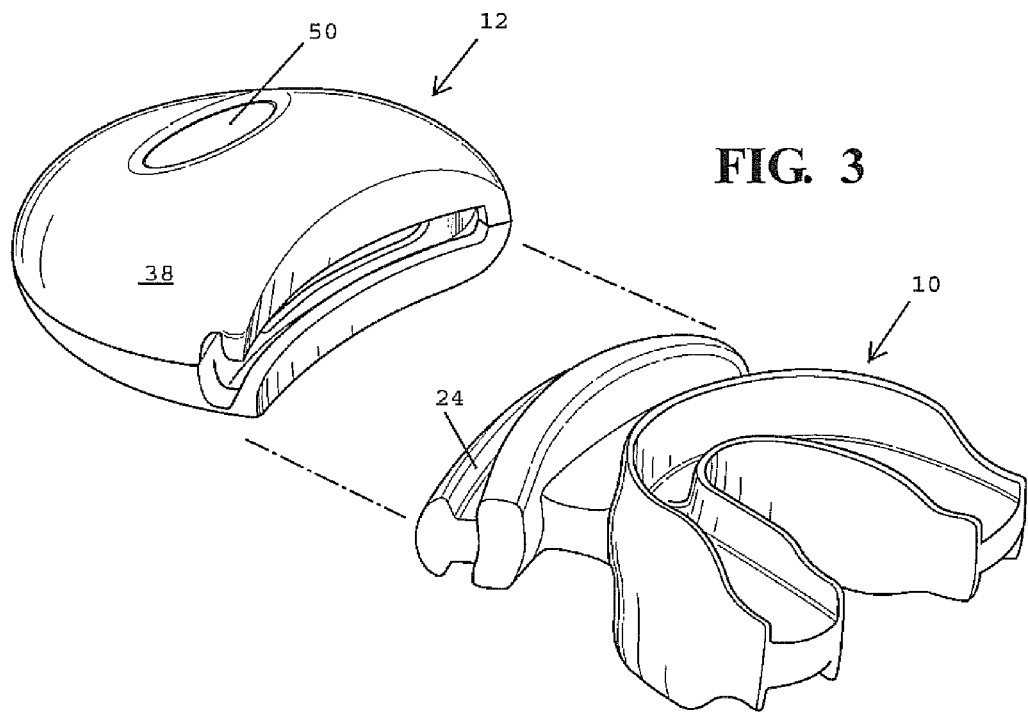
FIG. 3 is a similar perspective view with the two sections separated from one another.
Figure 4:
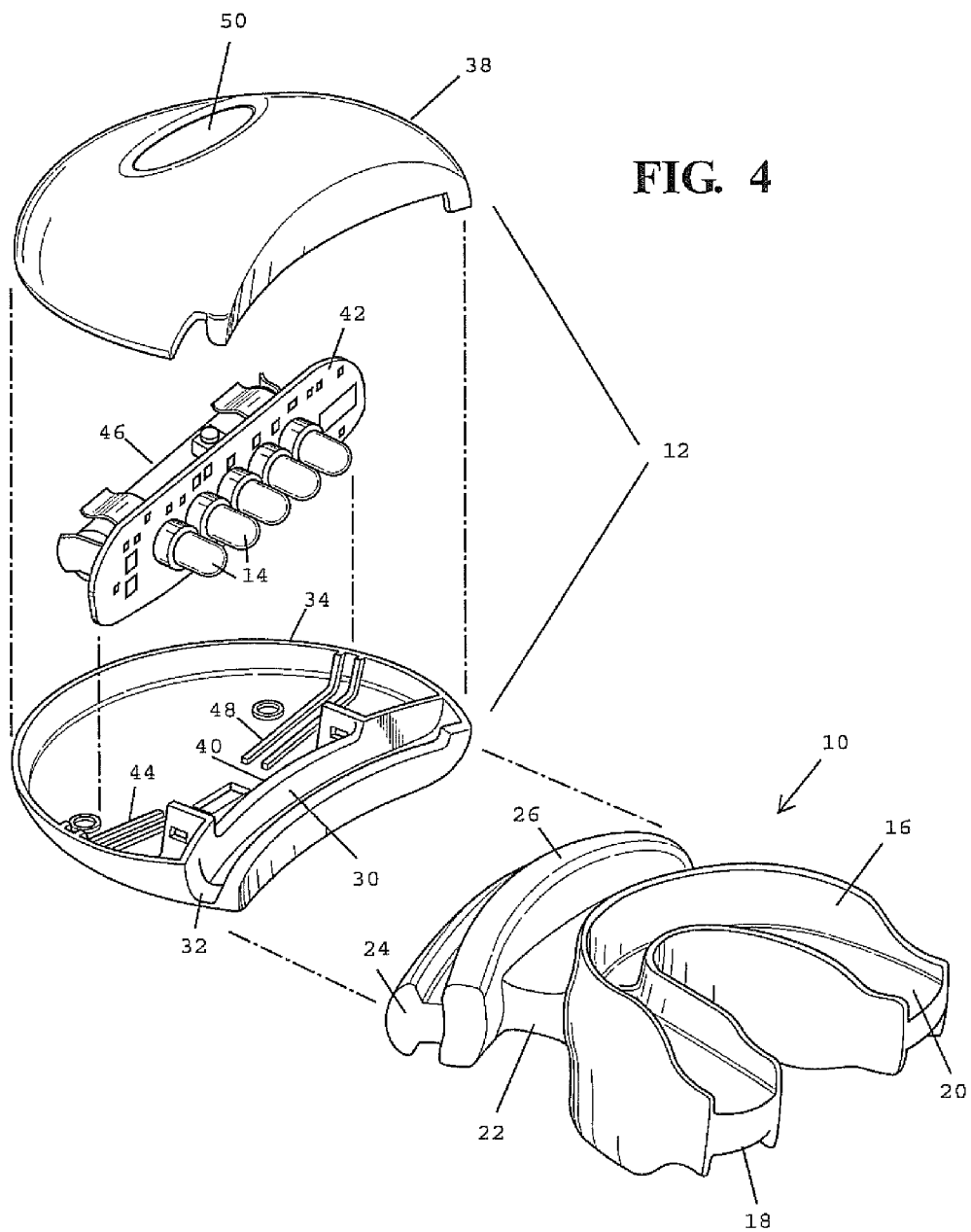
FIG. 4 is a view similar to FIG. 3 in which the components of the light box are shown in exploded view.
Figure 5:
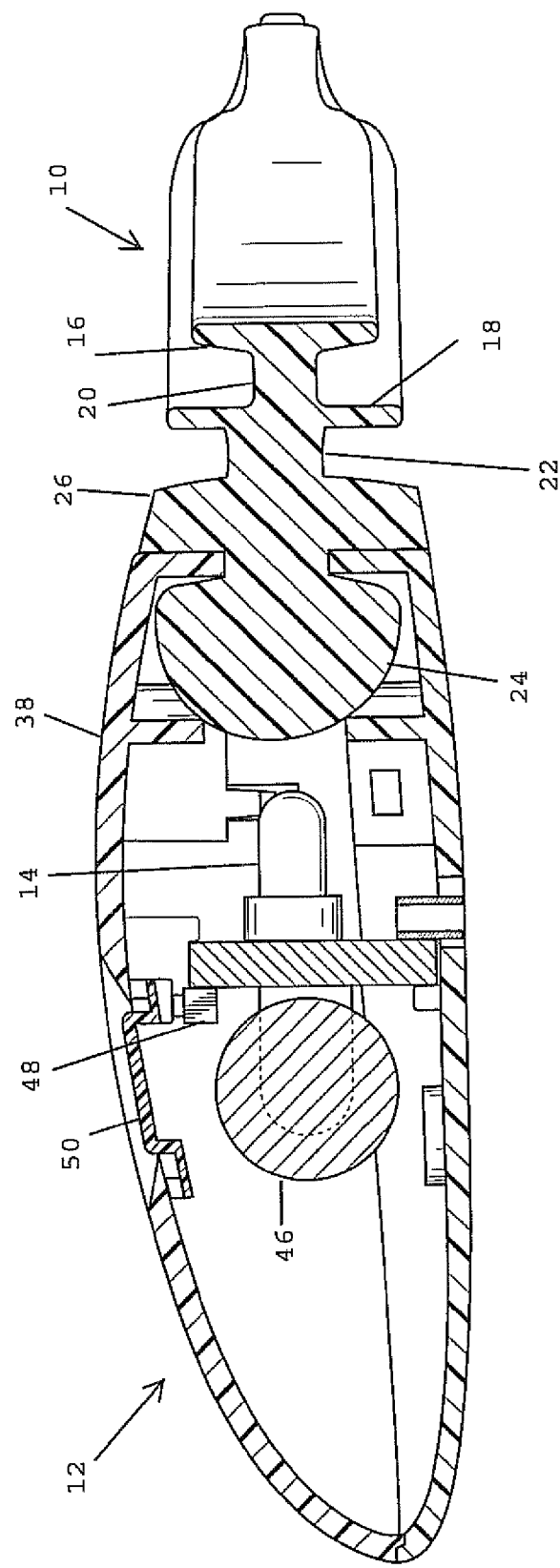
FIG. 5 is an enlarged longitudinal cross section through the preferred embodiment of the invention.

Referring to the drawings, the preferred embodiment of the device of the present invention generally comprises two components, a tray with a general U-shaped mouth trough, generally indicated at 10, and a light box, generally indicated at 12. The two units may be joined together as illustrated in FIG. 2 or separated from one another as illustrated in FIG. 3. The light box 12 preferably employs a series of five blue LEDs 14, best seen in FIG. 4, and accordingly the plastic used for the trough 10 is particularly transparent to light in the 450-500 nm wavelength generated by blue lasers 14.

Figure 1:
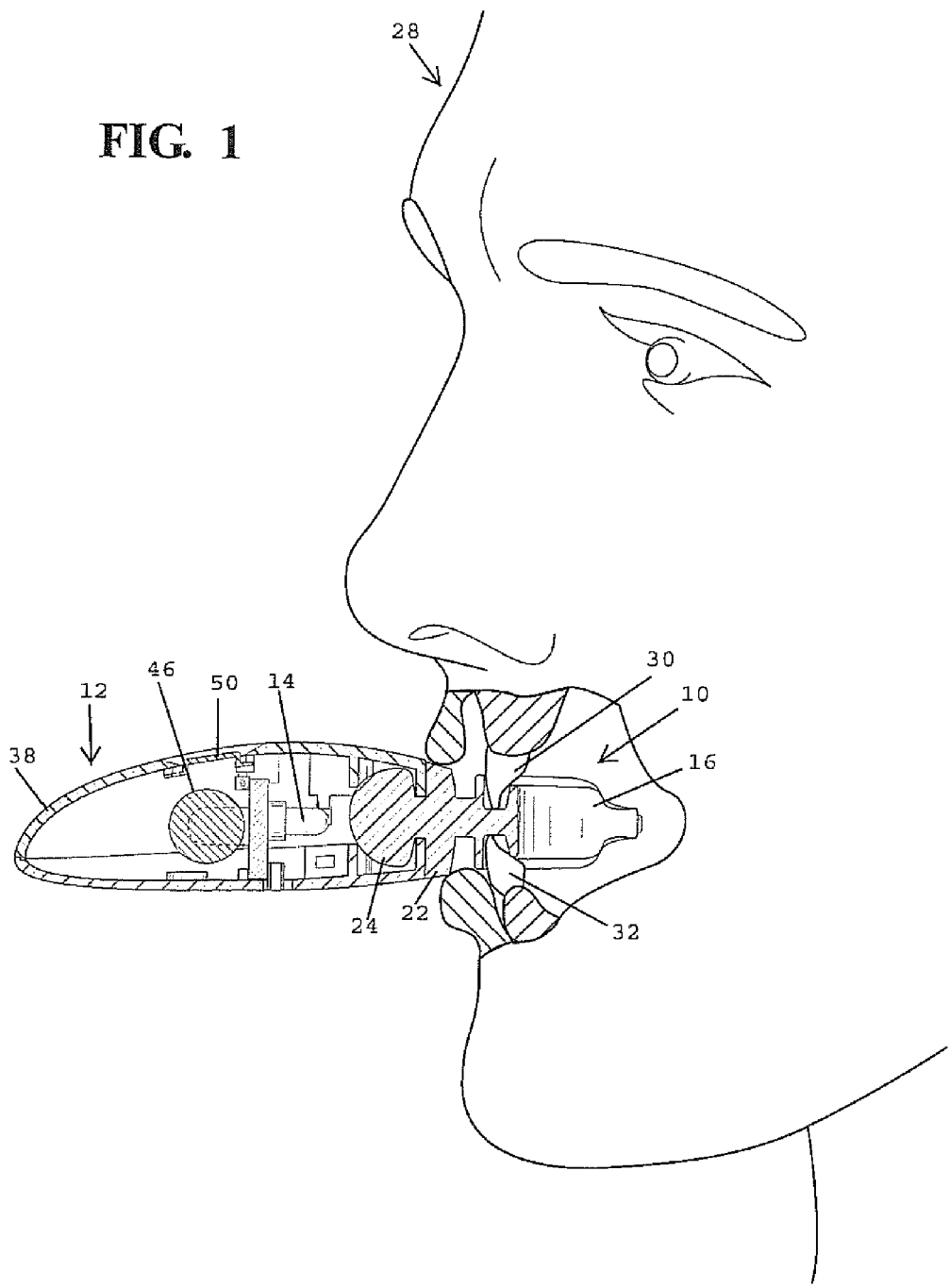
FIG. 1 is a semi schematic view of a user's mouth while employing the preferred embodiment of the invention, shown in cross section.

The mouth tray 10 generally comprises a horseshoe configuration with an upper trough section 16 and a lower trough section 18 which are configured to accommodate the upper and lower dental ridges of a user as generally illustrated at 28 in FIG. 1. The upper and lower trough sections 16 and 18 have a common planar base 20. At the forward side of the trough, in the same plane as the base 20, a forward projection 22 terminates at its far end with a male connecting section 24 comprising a section, convex in cross section, and curved in a convex manner in the plane of the base 20. The projecting section 22 and the male coupling section 24 are separated by a vertically projecting curved section 26 which extends above and below the plane of the base 20 and the connecting section 22. In the preferred embodiment of the invention the plastic used for the mouth tray 10 and projection 22 is a urethane, substantially transparent to the wavelength of the LEDs, such as BASF Elastollan 1170A.

As is best seen in FIG. 1, the tray 10, in use, is disposed within the user's mouth with the user's upper and lower teeth 30 and 32 extending into the upper and lower trough sections 16 and 18 respectively, with the ends of the teeth abutting the top and the bottom surfaces of the base 20. Previous to insertion of the trough within the user's mouth the troughs will be partially filled with a material, usually in gel form, which will break down to produce hydrogen peroxide which acts to oxidize and whiten inter-prismatic extrinsic staining formed on the tooth enamel.

Although any of a wide range of gels which are commercially available may be used with the invention, a preferred gel is carbamide peroxide, also termed urea hydrogen peroxide, blended with percarbamide, an oxidizing agent. The molecular formula for this gel is $CH_6N_2O_3$ or $CH_4N_2O.H_2O_2$. It is a white crystalline solid that releases oxygen in contact with water. This peroxide oxidizing agent is preferably used in combinations below about 30% carbamide peroxide (10% hydrogen peroxide equivalent) and at least 10% carbamide peroxide. The most preferred formula is 22% carbamide peroxide (7% hydrogen peroxide equivalent).

While the preferred embodiment contains the complementary troughs 16 and 18, so as to operate upon both the upper and lower dental ridges, in alternative embodiments of the invention only a single trough could be employed so as to make it useful for either the upper or lower dental ridges, but not both simultaneously. The gel contained within the dental trough decomposes at an accelerated rate when subjected to light from the LEDs 14, or alternative light sources, to substantially reduce the time required for a brightening session.

In use, as illustrated in FIG. 1, the user's teeth 30 are disposed within the trough or troughs which have been previously filled with gel so that they coat the user's teeth. Alternatively, the gel could be applied to the teeth before they are put into the troughs, which would also contain some gel, to ensure full coverage of the teeth. The user's lips are positioned over the projection 22 between the inner wall of the section 26 and the outer wall of the troughs.

The mouth tray 10 may be assembled with the light box 12 either before the trough section is inserted in the user's mouth or afterward. The light box 12 mates with the section 24 of the mouth tray by means of a curved groove 30 that is open at one end 32 and closed at the other end by a side wall 34 of the light box. The groove 30 is curved in a complementary manner to the mouth tray extending section 24 so that one end of the trough may be inserted through the opening 32 and will snugly engage the convex projection 24 along their entire lengths of contact.

When the upper light cover section 38 is joined to the lower section, as illustrated in the figures, the front end of the channel 32 is fully closed off, but the rear wall of the channel has a cutaway section 40 that connects to the interior of the closed light box and allows light from the LEDs 14 to project along the length of the male connecting section 24. By virtue of the light-conducting ability of the plastic used in the trough 10, this conducts light into the trough walls and thus into the gel coating the user's teeth. The curvature of the connecting section 24 evenly distributes the light from the LEDs into the trough and the convex shape of the section 24 acts much like a lens to distribute the light.

This arrangement of putting the light source externally of a mouth and simply transmitting light into the mouth obviates the need to bring electric current into the mouth which is problematic.

The LEDs 14 are supported on and project from a printed circuit board 42 which is supported in slots 44 formed in both sections of the light box cover. The printed circuit board supports a 1.5 volt rechargeable battery 46 on the side opposite the LEDs 14. Circuitry on the PC board 42 includes a voltage multiplier which raises the voltage applied to the LEDs to approximately 4.5 volts, and conductors for recharging the battery from the exterior of the light box.

The energization of the LEDs from the PC board is controlled by a switch 48 supported on the PC board, which may be actuated by a pushbutton 50 supported in the top section 38 of the light box. The pushbutton 50 is pivoted at one of its ends and when depressed actuates the switch 40.

The devices of the present invention are thus simple in construction and easy to use without the need to accommodate electrical circuitry within the user's mouth.

Having thus described our invention, we claim:

1. A device useful for whitening teeth, comprising:
   a U-shaped mouth tray having a trough adapted to conform to a dental ridge comprising a substantially flat base and side walls extending substantially normally to said base, the trough being adapted to be disposed within a user's mouth with at least certain of the user's teeth within said trough;
   a generally flat projection lying in a plane parallel to the base of the trough and fixed to and extending from the outer side of the trough so that the end of the projection opposite the trough lies externally of the user's mouth when the user's teeth are disposed in the trough;
   both the trough and the projection being formed of a plastic substantially transparent to light of a predetermined wavelength;
   a light-generating box containing an illumination source for light including said predetermined wavelength; and
   complementary, separable coupling structures formed of plastic substantially transparent to light of said predetermined wavelength respectively formed on the external end of the projection lying externally of the user's mouth when the user's teeth are disposed in the trough and on the light-generating box whereby light of said predetermined wavelength generated by said illumination source passes through the flat projection and the trough and illuminates the user's teeth disposed in the trough, said complementary separable coupling structure on the external end of the flat projecting section being convex in a plane normal to the base and constituting the male member of the complementary coupling structure.

2. The device of claim 1, wherein said illumination source comprises a plurality of LEDs.

3. The device of claim 2, wherein the LEDs are blue LEDs.

4. The device of claim 1, wherein said predetermined wavelength constitutes from about 450 to 500 nm.

5. The device of claim 1 further comprising a second U-shaped trough sharing the base of said first U-shaped trough and having side walls extending in an opposite direction to the side walls of the first U-shaped trough, whereby both the upper and lower teeth of a user may be accommodated simultaneously in said trough.

6. The device of claim 1, wherein said complementary coupling structure on the light-generating box comprises a slot adapted to surround the convex projection on the external end of the flat projecting section and has a cutaway extending along its length through which the illumination generated by the light-generating box may pass to said male member and said trough.

7. The device of claim 6, wherein the illumination source for light including said predetermined wavelength comprises a group of LEDs arrayed along the length of said slot.

8. The device of claim 7, wherein said light-generating box encloses a battery operative to provide the generating voltage for said LEDs.

9. The device of claim 1, wherein the trough is formed of urethane plastic.

10. The device of claim 1, wherein the convex section acts as a light pipe to collect the illumination generated by the LEDs and direct it to the trough.

11. The device of claim 1, wherein said convex coupling structure on the external end of the flat projecting section is integral with a connecting section extending normally to said trough base to form a platform to accommodate the user's lips.

12. The device of claim 1, wherein the U-shaped trough is shaped to accommodate a tooth whitening gel.

13. An apparatus useful in whitening teeth, comprising:

a U-shaped trough adapted to conform to a dental ridge having a base and extending side walls from opposite sides of the base and adapted to be disposed in a user's mouth to accommodate a gel-like substance for whitening teeth and a ridge of the user's teeth;

a generally flat projection joined to the outer side of the trough and adapted to project between the user's lips when the user's teeth are in the trough, the trough and the extension being formed of a plastic substantially transparent to light of a waveform which will accelerate curing of the gel; and a light box adapted to be disposed externally of the user's mouth and to illuminate the end of the projection opposite the end joined to the trough, the light box containing an illumination source for light of the wavelength adapted to accelerate action of the gel.

* * * * *